US009808498B2

(12) United States Patent
Giuliani et al.

(10) Patent No.: US 9,808,498 B2
(45) Date of Patent: Nov. 7, 2017

(54) FLAVONOID-BASED COMPOSITION FOR PHARMACEUTICAL, NUTRITIONAL OR COSMETIC USE HAVING POTENTIATED ANTIOXIDANT ACTION

(71) Applicant: GIULIANI S.P.A., Milan (IT)

(72) Inventors: Giammaria Giuliani, Milan (IT); Anna Benedusi, Milan (IT); Barbara Marzani, Carbonara al Ticino (IT); Antonio Mascolo, Milan (IT); Antonio Limitone, Milan (IT); Sergio Baroni, Villa D'adda (IT)

(73) Assignee: Giuliani S.p.A., Milan (IT)

( * ) Notice: Subject to any disclaimer, the term of this patent is extended or adjusted under 35 U.S.C. 154(b) by 0 days.

(21) Appl. No.: 14/777,181

(22) PCT Filed: Mar. 14, 2014

(86) PCT No.: PCT/EP2014/055162
§ 371 (c)(1),
(2) Date: Sep. 15, 2015

(87) PCT Pub. No.: WO2014/140312
PCT Pub. Date: Sep. 18, 2014

(65) Prior Publication Data
US 2016/0030500 A1 Feb. 4, 2016

(30) Foreign Application Priority Data
Mar. 15, 2013 (IT) ................. M12013A0397

(51) Int. Cl.
| | | |
|---|---|---|
| *A61K 36/87* | (2006.01) | |
| *A61K 45/06* | (2006.01) | |
| *A61K 31/05* | (2006.01) | |
| *A61K 31/353* | (2006.01) | |
| *A61K 36/63* | (2006.01) | |
| *A61K 8/49* | (2006.01) | |
| *A61Q 19/08* | (2006.01) | |
| *A61K 8/97* | (2017.01) | |
| *A61K 8/19* | (2006.01) | |
| *A61K 8/23* | (2006.01) | |
| *A61K 8/27* | (2006.01) | |

(Continued)

(52) U.S. Cl.
CPC ............ *A61K 36/87* (2013.01); *A23L 33/105* (2016.08); *A61K 8/19* (2013.01); *A61K 8/23* (2013.01); *A61K 8/27* (2013.01); *A61K 8/345* (2013.01); *A61K 8/498* (2013.01); *A61K 8/4973* (2013.01); *A61K 8/602* (2013.01); *A61K 8/97* (2013.01); *A61K 9/0012* (2013.01); *A61K 9/0014* (2013.01); *A61K 31/047* (2013.01); *A61K 31/05* (2013.01); *A61K 31/353* (2013.01); *A61K 31/355* (2013.01); *A61K 31/375* (2013.01); *A61K 31/7048* (2013.01); *A61K 33/04* (2013.01); *A61K 33/30* (2013.01); *A61K 33/34* (2013.01); *A61K 36/06* (2013.01); *A61K 36/63* (2013.01); *A61K 45/06* (2013.01); *A61Q 5/00* (2013.01); *A61Q 19/00* (2013.01); *A61Q 19/08* (2013.01); *A23V 2002/00* (2013.01); *A61K 2800/522* (2013.01); *A61K 2800/5922* (2013.01); *A61K 2800/92* (2013.01); *A61Q 5/02* (2013.01); *A61Q 7/00* (2013.01)

(58) Field of Classification Search
CPC ........ A61K 36/87; A61K 45/06; A61K 31/05; A61K 31/353; A61K 36/63; A61K 8/498; A61K 8/97; A61K 2800/522; A61K 2800/92; A61K 8/19; A61K 8/23; A61K 8/27; A61K 8/345; A61K 8/4973; A23V 2002/00; A61Q 5/02; A61Q 7/00; A61Q 19/08
See application file for complete search history.

(56) References Cited

U.S. PATENT DOCUMENTS

2009/0232942 A1* 9/2009 Degre .................. A23L 1/3016
426/62

FOREIGN PATENT DOCUMENTS

| DK | EP1790234 | * | 5/2007 | ............... A23K 1/14 |
|---|---|---|---|---|
| EP | 1790234 A1 | | 5/2007 | |

(Continued)

OTHER PUBLICATIONS

O. Benavente-Garcia, et al, Antioxidant Activity of Phenolics Extracted from *Olea europaea* L. Leaves, 68 Food Chem. 457 (2000).*

(Continued)

*Primary Examiner* — Sean Basquill
(74) *Attorney, Agent, or Firm* — LeClairRyan, a Professional Corporation

(57) ABSTRACT

The invention relates to a composition for pharmaceutical or nutritional or cosmetic use, formulated for oral or topical use and possessing antioxidant activity against free radicals, comprising: a) a *Vitis vinifera* seed, or seed and leaf, extract containing a combination of the flavonoids catechin and quercetin in a molar ratio in a range from 6:1 to 3:1, respectively, or a') a *Vitis vinifera* seed, or seed and leaf, extract containing a combination of the flavonoids catechin and quercetin in a molar ratio in a range from 7:1 to 4:1, respectively, or a") a mixture of *Vitis vinifera* extracts a) and a'), or a''') a mixture of catechin and quercetin in a molar ratio in a range from 7:1 to 3:1, respectively, together with b) an olive, *Olea europaea* L, leaf extract having a hydroxytyrosol content in a range from 1% to 30% by weight of the extract, or b') hydroxytyrosol in an amount equal to that contained in the b) extract.

17 Claims, 1 Drawing Sheet

(51) Int. Cl.

| | |
|---|---|
| *A61K 8/34* | (2006.01) |
| *A61K 8/60* | (2006.01) |
| *A61K 9/00* | (2006.01) |
| *A61K 31/047* | (2006.01) |
| *A61K 31/355* | (2006.01) |
| *A61K 31/375* | (2006.01) |
| *A61K 31/7048* | (2006.01) |
| *A61K 33/04* | (2006.01) |
| *A61K 33/30* | (2006.01) |
| *A61K 33/34* | (2006.01) |
| *A61K 36/06* | (2006.01) |
| *A61Q 5/00* | (2006.01) |
| *A61Q 19/00* | (2006.01) |
| *A23L 33/105* | (2016.01) |
| *A61Q 5/02* | (2006.01) |
| *A61Q 7/00* | (2006.01) |

(56) References Cited

FOREIGN PATENT DOCUMENTS

| EP | 2364697 A1 | 9/2011 |
|---|---|---|
| FR | 2942224 A1 | 8/2010 |
| IT | WO02/34262 * 5/2002 | ............ A61P 9/00 |
| WO | 02/34262 A1 | 5/2002 |
| WO | WO02/34262 * 5/2002 | ............ A61P 9/00 |

OTHER PUBLICATIONS

Leelavinothan Pari & Arumugam Suresh, Effect of Grape (*Vitis vinifera* L.) Leaf Extract on Alcohol Induced Oxidative Stress in Rats, 46 Food Chem. Toxicol. 1627 (2008).*

Antonella De Leonardo, et al, Isolation of a Hydroxytyrosol-rich Extract from Olive Leaves (*Olea europaea* L.) and Evaluation of its Antioxidant Properties and Bioactivity, 226 Eur. Food Res. Technol. 653 (2008).*

PCT International Search Report and Written Opinion for corresponding PCT/EP2014/055162, dated Mar. 14, 2014 (mailed Jun. 20, 2014).

PCT International Preliminary Report on Patentability for corresponding PCT/EP2014/055162, dated Mar. 14, 2014 (mailed Mar. 4, 2015).

Florence, "The Role of Free Radicals in Disease," Australia and New Zealand Journal of Ophthalmology 23(1):3-7 (1995).

Pala and Gurkan, "The Role of Free Radicals in Ethiopathogenesis of Diseases," Advances in Molecular Biology 1:1-9 (2008).

* cited by examiner

FLAVONOID-BASED COMPOSITION FOR PHARMACEUTICAL, NUTRITIONAL OR COSMETIC USE HAVING POTENTIATED ANTIOXIDANT ACTION

This application is a national stage application under 35 U.S.C. §371 of PCT Application No. PCT/EP2014/055162, filed Mar. 14, 2014, which claims the priority benefit of Italian Patent Application No. MI2013A000397, filed Mar. 15, 2013, which is hereby incorporated by reference in its entirety.

FIELD OF THE INVENTION

The subject of the present invention is a flavonoid-based composition for pharmaceutical, nutritional or cosmetic use having potentiated antioxidant action against free radicals.

PRIOR ART

Numerous studies demonstrate that the flavonoids, polyphenolic compounds present in nature as secondary metabolites in plants, possess an elevated antioxidant capacity against free radicals of oxygen (ROS), a well-known cause of degenerative diseases. Flavonoids are therefore indicated various applications in the medical field, for therapeutic as well as preventative purposes, for example in the treatment and prevention of cardiovascular disorders.

In the patent EP1328268 B1, the same Applicant, having summarised various of these studies as the prior art, describes a composition for pharmaceutical or dietetic use which has antioxidant activity, containing as the active principle a combination of the flavonoids catechin and quercetin, in a molar ratio in a range from 6:1 to 3:1, respectively. In particular, this combination of the two flavonoids obtained from an extract of a mixture of specific parts of *Vitis vinifera*, namely the seeds and the leaves, containing an average approximately 7.5 g of catechin and 1.5 g of quercetin per 100 g of extract. Among the indicated uses for this antioxidant composition, the patent proposes use as a platelet aggregation inhibitor in the treatment and prevention of cardiovascular disorders, the treatment and prevention of mental deterioration in old age, and the treatment and prevention of ageing of the skin.

French patent application 2947179 describes a composition having antioxidant properties comprising polyphenols obtained from a mixture of a grape extract rich in the flavonoid resveratrol and extract of the skin (epicarp or exocarp) of olives which is rich in maslinic acid, a triterpenoid $C_{30}H_{48}O_4$, described therein as a protease inhibitor; selenium induced in proteins of the alga spirulina; vitamin E; the enzyme superoxide dismutase (SOD).

DESCRIPTION OF THE INVENTION

This patent application compares the antioxidant capacity, or coefficient, of said polyphenols included in the composition, taken as such, i.e. substantially resveratrol and maslinic acid in admixture with each other, and of the composition itself, defined in this test (see the graph in FIG. 1) as a cocktail, that is, as a mixture of all the said ingredients, and it is found that this antioxidant capacity increases through the addition of the polyphenols of the other ingredients. According to the present invention, it is now being found that extracts of *Vitis vinifera* containing selected polyphenols, such as an extract of a mixture of seeds and leaves containing a combination of catechin and quercetin in a molar ratio within a defined interval as described in EP1328268, are capable of expressing a synergistically potentiated antioxidant action if an extract of leaves of the olive *Olea europea* L. having a content of hydroxytyrosol between 1% and 30% by weight of the extract is combined with these extracts.

As an alternative, the invention provides for use of analogous mixtures of the polyphenols catechin, quercetin and hydroxytyrosol as present in these extracts, in accordance with the same quantities.

The subject of the present invention is therefore a composition for pharmaceutical or nutritional or cosmetic use, possessing antioxidant activity against free radicals, comprising:

a) a *Vitis vinifera* seed, or seed and leaf, extract containing a combination of the flavonoids catechin and quercetin in a molar ratio in a range from 6:1 to 3:1, respectively, or a') a *Vitis vinifera* seed, or seed and leaf, extract containing a combination of the flavonoids catechin and quercetin in a molar ratio in a range from 7:1 to 4:1, respectively, or a") a mixture of *Vitis vinifera* extracts a) and a'), or a'") a mixture of catechin and quercetin in a molar ratio in a range from 7:1 to 3:1, respectively, together with b) an olive, *Olea europaea* L., leaf extract having a hydroxytyrosol content in a range from 1% to 30% by weight of the extract, or b') hydroxytyrosol in an amount equal to that contained in the b) extract.

Therefore the preferred embodiments of the invention are the following compositions, with reference to the said extracts a), a') a)'" of *Vitis vinifera*, and b) of olive, *Olea europaea* L.:

a)+b)
a')+b)
a")+b), or the following compositions, with reference to the ingredients a'") and b'):

a'")+b)
a)+b')
a')+b')
a")+b')
a'")+b')

In the embodiment providing for a"): a mixture of *Vitis vinifera* extracts a) and a'), catechin and quercetin are preferably present in the composition in a molar ratio generally within a range from 7:1 to 3:1, respectively.

According to a different embodiment of the invention, the composition also comprises: c) selenium, preferably in the form of selenium-enriched yeast.

Other embodiments of the invention may comprise other known compounds having antioxidant activity, for example zeaxanthin, rutin, ascorbic acid, vitamin E, zinc, copper.

Said olive, *Olea europaea* L., leaf extract b) has a content of hydroxytyrosol in a range from 1% to 30% by weight of the extract, preferably from 5% to 30%, yet more preferably at least 10%.

As a bibliographical reference to characterise the olive, *Olea europaea* L., leaf extract b) according to the composition of the invention, one may cite Benavente-Garcia et al., Antioxidant activity of phenolics extracted from *Olea europaea* L. leaves, Food Chemistry, vol. 68, no. 4, pp. 457-462, 2000, wherein is described a mixture of the following flavonoids with related absolute percentage content on dry basis (% d.s.):

| | |
|---|---|
| Hydroxytyrosol | 1.46 |
| Tyrosol | 0.71 |
| Catechin | 0.04 |
| Caffeic acid | 0.34 |
| Vanillic acid | 0.63 |
| Vanillin | 0.05 |
| Rutin | 0.05 |
| Luteolin-7-glucoside | 1.38 |
| Verbascoside | 1.11 |
| Apigenin-7-glucoside | 1.37 |
| Diosmetin-7-glucoside | 0.54 |
| Oleuropein | 24.54 |
| Luteolin | 0.21 |
| Diosmetin | 0.05 |

The said *Vitis vinifera* seed, or seed and leaf, extract a) containing a combination of the flavonoids catechin and quercetin in a catechin/quercetin molar ratio in a range from 6:1 to 3:1 is preferably a dry extract having a total polyphenol content higher than 60%, and 15-20% oligomeric proanthocyanidins (OPC), obtained using ethanol/water as the extraction solvent.

The *Vitis vinifera* seed, or seed and leaf, extract a') containing a combination of the flavonoids catechin and quercetin in a catechin/quercetin molar ratio in a range from 7:1 to 4:1 is preferably a dry extract having a total polyphenol content higher than 95%, and oligomeric proanthocyanidins (OPC) higher than 30%, extraction solvent ethanol/water.

A preferred extract according to a) and a') is taken from seeds and leaves of *Vitis vinifera* containing a combination of the flavonoids catechin and quercetin in a molar ratio equal to approximately 5:1, respectively.

In what follows, a number of non-limiting examples of composition according to the invention, formulated for oral or topical use are described.

Topical use provides for an application of the composition on the skin or on the hair.

In the examples which follow, each active ingredient extract according to the invention is identified by the symbols a), a'), b) and c) as defined above more in general.

Example 1

DIETETIC PRODUCT- TABLET - Composition a') + b) + c)

| Ingredient | quantity u.m. |
|---|---|
| Granular L-methionine | 300 mg |
| Spermidine trihydrochloride | 0.50 mg |
| Zeaxanthin | 2.00 mg |
| Rutin | 2.50 mg |
| Calcium d-pantothenate | 9.0 mg |
| d-Biotin | 0.050 mg |
| Ascorbic acid | 90.0 mg |
| Vitamin E acetate | 15.0 mg |
| Pyridoxine hydrochloride | 2.43 mg |
| Zinc bisglycinate | 26.6 mg |
| Copper bisglycinate | 4.0 mg |
| Folic acid | 0.30 mg |
| Dry extract of *Vitis vinifera* L . . . ingredient a') | 60.0 mg |
| Extract of olive *Olea europea* L . . . ingredient b) | 10.0 mg |
| Selenium-enriched yeast ingredient c) | 15.0 mg |
| Croscarmellose sodium | 25.0 mg |
| Dicalcium phosphate | 25.0 mg |
| Microcrystalline cellulose | 65.0 mg |
| Magnesium stearate | 8.0 mg |
| Silicon dioxide | 5.0 mg |

Example 2

DIETETIC PRODUCT - TABLET - Composition a) + b)

| Ingredient | quantity u.m. |
|---|---|
| Dry extract of *Vitis vinifera*, a) | 30.0 mg |
| Olive *Olea europea* L. extract), b) | 10.0 mg |
| Dicalcium phosphate | 300.0 mg |
| Microcrystalline cellulose | 300.0 mg |
| Mixture of behenic acid mono-, di-and triglycerides | 8.0 mg |
| Silicon dioxide | 5.0 mg |

Example 3

DIETETIC PRODUCT - HARD GELATIN CAPSULE - Composition a') + b)

| Each hard gelatin capsule contains: | quantity u.m. |
|---|---|
| Dry extract of *Vitis vinifera* L., a') | 30.0 mg |
| Olive *Olea europea* L. extract, b) | 5.0 mg |
| Maltodextrin | 50.0 mg |
| Magnesium stearate | 2.0 mg |
| Silicon dioxide | 3.0 mg |
| Natural gelatin | Outer shell |

Example 4

DIETETIC PRODUCT - ORAL GRANULATE - Composition a') + b)

| Each sachet contains: | quantity u.m. |
|---|---|
| Dry extract of *Vitis vinifera* L., a') | 40.0 mg |
| Olive *Olea europea* L. extract, b) | 10.0 mg |
| Fructose | 0.445 g |
| Maltodextrin | 1.50 g |
| Flavouring | 10.0 mg |
| Sucralose | 0.005 mg |

Example 5

SHAMPOO - Composition a') + b)

| Ingredient (INCI name) | quantity p/p (%) |
|---|---|
| Disodium Laureth Sulfosuccinate | 1.00-5.00 |
| Magnesium Laureth Sulfate | 5.00-9.00 |
| PEG-7 Glyceryl Cocoate | 0.50-1.00 |
| Cocamide MIPA | 0.50-2.00 |
| Peg-200 Hydrogenated Glyceryl Palmate | 0.50-2.00 |
| Polyquaternium-10 | 0.10-0.50 |
| Tetrasodium EDTA | 0.05-0.20 |
| Sodium Lauroyl Sarcosinate | 1.00-4.00 |
| Tetrasodium EDTA | 0.05-0.20 |
| Dry extract of *Vitis vinifera* L., a') | 0.12-0.03 |
| Olive *Olea europea* L. extract, b) | 0.04-0.005 |
| BHA | 0.005-0.015 |
| Potassium Undecilenoyl Wheat Protein | 0.50-1.00 |
| Phenyl Trimethicone | 0.5-1.50 |
| Silicone Quaternium-15 | 0.01-0.07 |
| Laureth-4 | 0.01-0.80 |
| Fragrance | 0.10-0.80 |
| Glycol Distearate | 0.50-1.00 |

-continued

| SHAMPOO - Composition a') + b) | |
|---|---|
| Ingredient (INCI name) | quantity p/p (%) |
| Laureth-7 | 0.50-0.80 |
| Sodium Cocoamphoacetate | 0.05-3.00 |
| Cocamidopropyl Betaine | 0.01-2.00 |
| Sodium Laureth Sulfate | 0.01-3.00 |
| Sodium Hydroxymethylglycinate | 0.20-0.45 |
| Benzoic acid | 0.005-0.10 |
| Sodium hydroxyde | q.s. |
| Citric acid | q.s. |
| Aqua | q.s. ad 100.00 |

Example 6

| MEDIUM PROTECTION SUN CARE PRODUCT - Composition a') + b) | |
|---|---|
| Ingredient (INCI name) | quantity p/p (%) |
| Propylene glycol | 1.00-5.00 |
| C12-15 alkyl benzoate | 5.00-7.00 |
| Ethylexyl methoxycinnamate | 3.00-7.00 |
| Dry extract of *Vitis vinifera* L., a') | 0.12-0.03 |
| Olive *Olea europea* L. extract, b) | 0.04-0.005 |
| Isostearyl isostearate | 2.00-8.00 |
| Styrene/Acrylates Copolymer | 1.00-5.00 |
| Acrylates/C10-30 Alkyl Acrylate Crosspolymer | 0.05-0.70 |
| Butylene glycol cocoate | 1.00-5.00 |
| Butyl methoxydibenzoylmethane | 1.00-5.00 |
| Hydroxybenzoyl Hexyl Benzoate diethylamine | 1.00-5.00 |
| Ethylhexyl Triazone | 1.00-5.00 |
| Octocrylene | 1.00-5.00 |
| PPG-15 stearyl ether | 1.00-5.00 |
| Diethylhexyl syringylidene malonate | 0.10-1.00 |
| Sorbityl furfural | 0.05-0.10 |
| Ethylhexylglycerin | 0.15-0.60 |
| Polyperfluoroethoxymethoxy Difluoroethyl PEG Phosphate | 0.2-1.50 |
| Fragrance | 0.1-0.5 |
| Phenoxyethanol | 0.80-1.00 |
| Sodium Hydroxide | q.s |
| Aqua | q.s. ad 100.00 |

Example 7

| HAIR LOSS LOTION - Composition a') + b) | |
|---|---|
| Componente (INCI name) | quantity p/p (%) |
| Denat. alcohol | 10.00-30.00 |
| Disodium EDTA | 0.025-0.20 |
| Dry extract of *Vitis vinifera* L., a') | 0.12-0.03 |
| Olive *Olea europea* L. extract., b) | 0.04-0.005 |
| Biotin | 0.001-0.005 |
| Fragrance | 0.30 |
| *Ajuga reptans* leaf extract | 0.01-0.05 |
| Calcium pantothenate | 0.05-0.40 |
| PEG-40 Hydrogenated Castor Oil | 0.20-1.00 |
| Aqua | q.s. ad 100.00 |

Example 8

| FACE CREAM - Composition a) + b) + c) | |
|---|---|
| Ingredient (INCI name) | quantity p/p (%) |
| Glycerin | 2.00-5.00 |
| Diglycerin | 0.20-2.00 |
| Cetearyl alcohol | 0.20-2.50 |
| Cetearyl glucoside | 0.20-2.50 |
| PEG-100 Stearate | 0.20-1.00 |
| Sorbityl furfural | 0.5-1.00 |
| Tetrasodium Glutamate Diacetate | 0.10-0.50 |
| Dry extract of *Vitis vinifera* L., a) | 0.24-0.06 |
| Olive *Olea europea* L. extract, b) | 0.04-0.01 |
| Selenium-enriched yeast, ingredient c) | 0.06-0.015 |
| Palm butter | 0.50-3.00 |
| Hydrogenated Evening Primrose Oil | 0.50-3.00 |
| Octyldodecanol | 0.50-3.00 |
| Hydrogenated castor oil | 1.00-4.00 |
| Ethylhexyl cocoate | 1.00-4.00 |
| Acrylates/C10-30 Alkyl acrylate crosspolymer | 1.00-2.00 |
| *Butyrospermum parkii* | 1.00-5.00 |
| Beta sitosterol | 0.10-0.50 |
| Tocopherol | 0.05-0.20 |
| Dimethicone | 0.50-1.50 |
| Dimethicone crosspolymer | 0.10-1.50 |
| Ethylhexylglycerin | 0.25-0.50 |
| Phenoxyethanol | 0.50-0.99 |
| Fragrance | q.s. |
| Aqua | q.s. ad 100.00 |

Experimental Part—ORAC Test

Method

The antioxidant activity was measured as the ORAC (oxygen radical absorbance capacity) in accordance with the following test.

The ORAC test was performed according to the method described by Ou, Hampsch-Woodill and Prior, "Development and validation of an improved oxygen radical absorbance capacity assay using fluorescein as the fluorescent probe", J Agric Food Chem 49 (10): 4619-26, (2001), with a number of modifications as described by Duais, Müller et al. (2009). The fluorescent probe used was fluorescein diluted in PBS (Phosphate buffered saline) (75 mmol/L, pH 7.4). A working solution equivalent to 1.2 µmol/L, fresh preparation from a 120 µmol/L stock solution stored in a refrigerator, was used for the analyses. The filters used in the microplate reader were a 485 nm filter (excitation) and a 520 nm filter (emission). The reaction was conducted in PBS 75 mmol/L (pH 7.4).

The following were pipetted into each well of the microplate: 10 µL of aqueous sample diluted as described below, 100 µL of PBS e 25 µL of the fluorescein solution (1.2 µmol/L) and preheated for 10 minutes at 37° C. Water was used as a blank and experimental control. However, for the calibration curve, Trolox (0.1-2.5 mmol/L) was used as a standard. The reaction starts with addition of a 129 mmol/L solution of AAPH (2,2'-azobis(2-amidino-propane) dihydrochloride) in PBS, freshly prepared and refrigerated on ice, and subsequent measurement of the fluoroscein for 2 h at 37° C. To check for the photostability of the fluoroscein, the same volume of PBS was added to a few of the wells.

To calculate the ORAC value, the relative fluorescence data at each minute were generated on the basis of the fluorescence intensity of the samples, the blank and the control. The area under the curve (AUC) was then calculated for each sample, equation (1):

$$AUC = 1 + \left(\frac{f_1 + f_2 + f_3 + \ldots f_i}{f_0}\right) \quad (1)$$

where $f_0$ represents the relative fluorescence at 0 minutes e $f_i$ the relative fluorescence at the time i. The $AUC_{net}$ was calculated by subtracting the AUC value of the blank from that of the sample or of the standard, equation (2):

$$AUC_{net} = AUC_{sample/standard} - AUC_{blank} \quad (2)$$

The final ORAC value, obtained from the $AUC_{net}$ value and the Trolox concentration with the use of a regression equation, is therefore expressed as Trolox® equivalents (TE) in mmol/100 g.

The value obtained is then subsequently converted into ORAC units (1 ORAC unit=1 μM of Trolox equivalents).

Samples

Using the test described here by way of example, the samples subjected to ORAC measurement were the extracts a) and b) as defined above, both individually as such for comparison purposes, and as compositions according to the present invention, as specified in what follows.

In particular, extract a) undergoing measurement herein is a dry extract of seeds and leaves of *Vitis vinifera* containing a combination of the flavonoids catechin and quercetin in a catechin/quercetin molar ratio equal to 5.2:1, respectively; total polyphenols>60% (UV), catechin 3.0% (HPLC), quercetin 0.6% (HPLC); extraction solvent ethanol/water.

The selected reference for comparison purposes was a dry extract of skin of the *Vitis vinifera* grape titrated into resveratrol, having a content of total polyphenols higher than 70%, of oligomeric proanthocyanidins higher than 15%, of resveratrol higher than 100 ppm, extraction solvent ethanol/water. This comparison extract is here defined by the symbol Ref.).

The following extracts were tested individually:
Extract of the seeds and leaves of *Vitis vinifera* a), 60 mg in quantity
Grape skin extract Ref.), 60 mg in quantity
Olive leaf extract b), 30 mg in quantity, symbol b)$_{30}$
Olive leaf extract b), 10 mg in quantity, symbol b)$_{10}$ The following compositions were tested: a)+b) according to the invention and Ref.)+b) as the reference for comparison purposes:
a)+b), where a): b) are in a ratio by weight equal to 6:3, respectively.
a)+b), where a): b)=6:1.
Ref.)+b), where Ref.): b)=6:3
Ref.)+b), where Ref.): b)=6:1

Results

The data obtained are presented in the table below, wherein ORAC is measured in micromoles of Trolox equivalent (TE) for weight of the sample, expressed in mg.

| | Ingredients and compositions | ORAC (TE micromoles over x mg) | Sum of ORAC individual ingredients | Variation in ORAC in compositions |
|---|---|---|---|---|
| a) | *Vitis vinifera* seeds and leaves extract, 60 mg | 212.4 | — | — |
| Ref.) | *Vitis vinifera* grape skin extract, 60 mg | 388.2 | — | — |
| b)$_{30}$ | Olive leaf extract 30 mg | 66.9 | — | — |
| b)$_{10}$ | Olive leaf extract 10 mg | 22.3 | — | — |
| a) + b)$_{30}$ | *Vitis vinifera* seeds and leaves + Olive leaf extract 30 mg 6:3 | 481.5 | 279.3 | +72% |
| a) + b)$_{10}$ | *Vitis vinifera* seeds and leaves + Olive leaf extract 10 mg 6:1 | 382.2 | 234.7 | +63% |
| Ref.) + b)$_{30}$ | *Vitis vinifera* grape skin + Olive leaf extract 30 mg 6:3 | 411.3 | 455.1 | −10% |
| Ref.) + b)$_{10}$ | *Vitis vinifera* grape skin + Olive leaf extract 10 mg 6:1 | 288.4 | 410.5 | −30% |

DESCRIPTION OF THE DRAWINGS

The data shown in table form are also presented graphically in FIGS. 1 and 2 of the attached drawings, which show on the ordinate the ORAC values measured in micromoles of trolox equivalent (TE) for the individual ingredients and for the respective compositions as here defined.

For the compositions of the invention a)+b)$_{30}$ and a)+b)$_{10}$, FIG. 1 shows an increase in ORAC of 72% and 63% respectively, with respect to the ORAC algebraic sum of the individual ingredients, extracts a) and b), therefore an increase of synergistic type.

Figure 1:
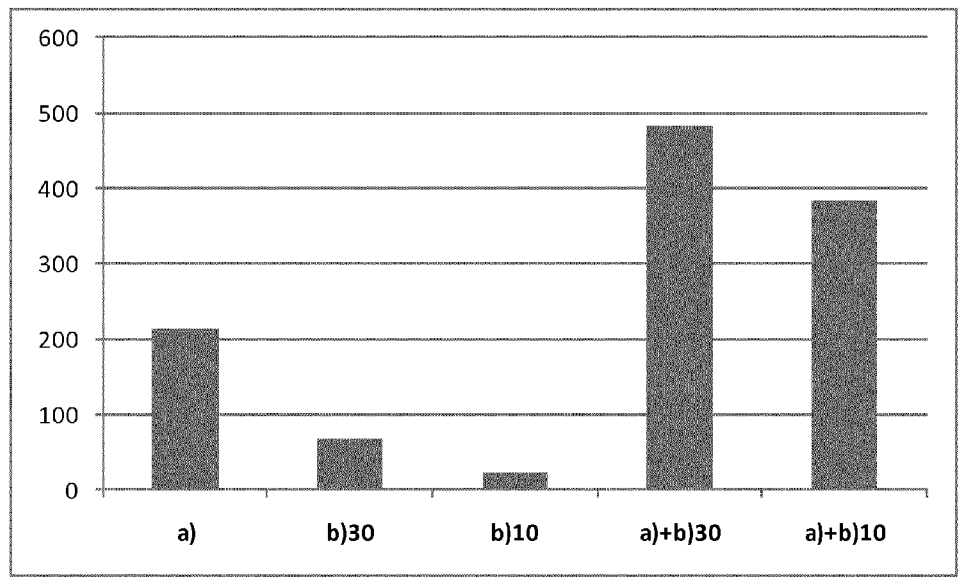
FIG. 1 relates to the comparison between the individual extracts a) of *Vitis vinifera* seeds and leaves, b)$_{30}$ and b)$_{10}$ of olive leaves as mentioned above, versus the respective compositions a)+b)$_{30}$ and a)+b)$_{10}$, in order.
Figure 2:
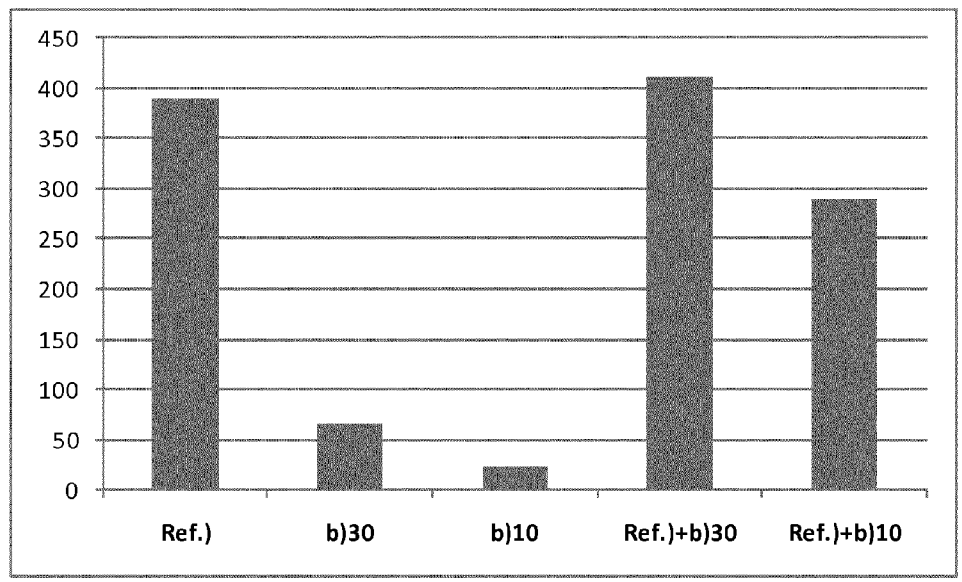
FIG. 2 relates to the comparison between individual Ref. extracts) of *Vitis vinifera* grape skin, b)$_{30}$ and b)$_{10}$ of olive leaves as mentioned above, versus the respective compositions Ref.)+b)$_{30}$ e Ref.)+b)$_{10}$, in order.

By contrast, for both the comparison compositions Ref.)+b)$_{30}$ and Ref.)+b)$_{10}$ we actually find a reduction (approximately −10% and −30%, respectively) in respect of the ORAC algebraic sum of the individual ingredients, extracts Ref. and b).

These experimental results demonstrate on the one hand the importance of selecting extracts of *Vitis vinifera* such as a), and similarly a') or a"), or of their synthetic analogue a"') according to the present invention, i.e. containing the polyphenols catechin and quercetin in a molar ratio within a specific range, as compared with other *Vitis vinifera* extracts such as Ref., which is an extract of skin of the *Vitis vinifera* grape titrated in resveratrol, a different polyphenol.

On the other hand, according to the present invention it must be considered totally surprising that the known antioxidant activity of the *Vitis vinifera* extracts in question can be synergistically potentiated by addition of an olive extract b), or of a synthetic analogue thereof b'), which as such has an inferior antioxidant activity as compared with each of the *Vitis vinifera* extracts discussed here, whether they are of the type a), or similar according to the invention, or Ref.), not part of the invention.

The invention claimed is:

1. Composition for pharmaceutical use having synergistic antioxidant activity against free radicals, comprising:
   a) a *Vitis vinifera* seed and leaf extract containing a combination of the flavonoids catechin and quercetin in a molar ratio in a range from 6:1 to 3:1, respectively, together with b) an olive, *Olea europaea* L., leaf extract having a hydroxytyrosol content in a range from 1% to 30% by weight of the extract.

2. Composition as claimed in claim 1, characterized in that said b) olive, *Olea europaea* L., leaf extract has a hydroxytyrosol content of at least 10%.

3. Composition as claimed in claim 1, characterized in that said b) olive leaf extract contains the following flavonoids, with related absolute percentage content on dry basis (% d.s.):

| | |
|---|---|
| Hydroxytyrosol | 1.46 |
| Tyrosol | 0.71 |
| Catechin | 0.04 |
| Caffeic Acid | 0.34 |
| Vanillic Acid | 0.63 |
| Vanillin | 0.05 |
| Rutin | 0.05 |
| Luteolin-7-glucoside | 1.38 |
| Verbascoside | 1.11 |
| Apigenin-7-glucoside | 1.37 |
| Diosmetin-7-glucoside | 0.54 |
| Oleuropein | 24.54 |
| Luteolin | 0.21 |
| Diosmetin | 0.05. |

4. Composition as claimed in claim 1, characterized in that said a) *Vitis vinifera* seed and leaf extract contains a combination of the flavonoids catechin and quercetin in a molar ratio in a range from 6:1 to 3:1, respectively, a total polyphenol content higher than 60% and oligomeric proanthocyanidins (OPC) between 15 and 20%, obtained by the extraction solvent ethanol/water.

5. Composition as claimed in claim 1, characterized in that it comprises selenium.

6. Composition as claimed in claim 5, characterized in that it comprises selenium in the form of selenium-enriched yeast.

7. Composition as claimed in claim 1, characterized in that it comprises at least an antioxidant selected from zeaxanthin, rutin, ascorbic acid, vitamin E, zinc, copper.

8. Composition as claimed in claim 1, characterized in that it is formulated for oral use.

9. Composition as claimed in claim 1, characterized in that it is formulated for topical use.

10. Composition as claimed in claim 9, characterized in that it is formulated for topical use on the skin.

11. Composition as claimed in claim 9, characterized in that it is formulated for topical use on the hair.

12. A method to produce antioxidant activity against free radicals for cosmetic purposes in a subject in need thereof, comprising:
    administering to the subject, orally or topically, a composition according to claim 1:
    wherein the ratio of a) or a''') to b) or b') is 6:1 to 6:3.

13. A method to produce antioxidant activity against free radicals for nutritional or dietetic purposes in a subject in need thereof comprising:
    administering to the subject, orally or topically, a composition according to claim 1:
    wherein the ratio of a) or a''') to b) or b') is 6:1 to 6:3.

14. The method according to claim 12, characterized in that the composition is formulated for oral use.

15. The method according to claim 12, characterized in that the composition is formulated for topical use.

16. The method according to claim 15, characterized in that the composition is formulated for topical use on the skin.

17. The method according to claim 15, characterized in that the composition is formulated for topical use on the hair.

\* \* \* \* \*

UNITED STATES PATENT AND TRADEMARK OFFICE
CERTIFICATE OF CORRECTION

PATENT NO.         : 9,808,498 B2
APPLICATION NO.    : 14/777181
DATED              : November 7, 2017
INVENTOR(S)        : Giuliani et al.

It is certified that error appears in the above-identified patent and that said Letters Patent is hereby corrected as shown below:

In Claim 12, at Column 10, Line 18, please delete ":" and insert --.--

In Claim 12, at Column 10, Line 19, please delete "wherein the ratio of a) or a'") to b) or b') is 6:1 to 6:3."

In Claim 13, at Column 10, Line 24, please delete ":" and insert --.--

In Claim 13, at Column 10, Line 25, please delete "wherein the ratio of a) or a'") to b) or b') is 6:1 to 6:3."

Signed and Sealed this
Twentieth Day of February, 2018

Andrei Iancu
*Director of the United States Patent and Trademark Office*